United States Patent [19]
Norman et al.

[11] Patent Number: 6,046,364
[45] Date of Patent: Apr. 4, 2000

[54] REGENERATION OF METAL CVD PRECURSORS

[75] Inventors: John Anthony Thomas Norman, Encinitas; John Cameron Gordon, Vista; Yoshihide Senzaki, Carlsbad, all of Calif.

[73] Assignee: Air Products and Chemicals, Inc., Allentown, Pa.

[21] Appl. No.: 09/206,427

[22] Filed: Dec. 7, 1998

[51] Int. Cl.⁷ ............... C07C 205/00; C07F 1/08
[52] U.S. Cl. ............ 568/306; 427/252; 427/587; 564/275; 564/278; 568/307; 568/331; 568/412; 556/117
[58] Field of Search ............ 568/412, 306, 568/307, 331; 564/275, 278; 556/117; 427/252, 587

[56] References Cited

U.S. PATENT DOCUMENTS

| | | | |
|---|---|---|---|
| 3,356,527 | 12/1967 | Moshier et al. | 117/107.2 |
| 3,594,216 | 7/1971 | Charles et al. | 117/107.2 |
| 5,085,731 | 2/1992 | Norman et al. | 156/646 |
| 5,098,516 | 3/1992 | Norman et al. | 156/666 |
| 5,144,049 | 9/1992 | Norman et al. | 556/12 |
| 5,187,300 | 2/1993 | Norman et al. | 556/12 |
| 5,322,712 | 6/1994 | Norman et al. | 427/250 |

OTHER PUBLICATIONS

Removal of Byproducts from CVD Copper Effluent Streams, No. 41242, Research Disclosures, (Aug. 1998), pp. 1059–1061.

Temple, et al., Chemical Vapor Deposition of Copper from Copper (II) Hexafluoracetylacetonate, J. Electrochem. Soc. vol. 136, No. 11, Nov. 1989, pp. 3525–3529.

Kaloyeros, et al., Low–Temperature Metal–Organic Chemical Vapor Deposition ((LTMOCVD) of Device–Quality Copper Films for Microelectronic Applications, J. Electr. Mat., vol. 19, No. 3, 1990, pp. 271–276.

Van Hemert, et al. Vapor Deposition of Metals by Hydrogen Reduction of Metal Chelates, J. Electrochem. Soc., vol. 112, No. 11, Nov. 1965, pp. 1123–1126.

Oehr, et al., Thin Copper Films by Plasma CVD Using Copper–Hexafluoro–Acetylacetonate, Appl. Phys., A 45, (1988), pp. 151–154.

*Primary Examiner*—Porfirio Nazario-Gonzalez
*Attorney, Agent, or Firm*—Geoffrey L. Chase

[57] ABSTRACT

A process for recovering a 1,1,1,5,5,5-hexafluoro-2,4-pentanedione ligand from a metal-ligand complex byproduct such as $Cu^{+2}(1,1,1,5,5,5\text{-hexafluoro-2,4-pentanedionate}^{-1})_2$, comprising: providing a copper-ligand complex byproduct of $Cu^{+2}(1,1,1,5,5,5\text{-hexafluoro-2,4-pentanedionate}^{-1})_2$ in a process stream; cooling and condensing the copper-ligand complex byproduct of $Cu^{+2}(1,1,1,5,5,5\text{-hexafluoro-2,4-pentanedionate}^{-1})_2$ to separate it from the process stream; contacting the copper-ligand complex byproduct of $Cu^{+2}(1,1,1,5,5,5\text{-hexafluoro-2,4-pentanedionate}^{-1})_2$ with a protonation agent, such as: sulfuric acid, hydrochloric acid, hydroiodic acid, hydrobromic acid, trifluoroacetic acid, trifluoromethanesulfonic acid, acid ion exchange resin, hydrogen sulfide, water vapor and mixtures thereof; and recovering 1,1,1,5,5,5-hexafluoro-2,4-pentanedione.

16 Claims, No Drawings

REGENERATION OF METAL CVD PRECURSORS

CROSS-REFERENCE TO RELATED APPLICATIONS

Not applicable.

STATEMENT REGARDING FEDERALLY SPONSORED RESEARCH OR DEVELOPMENT

Not applicable.

BACKGROUND OF THE INVENTION

Many processes used in semiconductor manufacturing involve the use of metal containing chemicals, or their solutions, for the purpose of depositing thin metallic films onto silicon wafer surfaces. Examples include the use of tungsten hexafluoride for tungsten metallization by Chemical Vapor Deposition (CVD), dimethylaluminum hydride for aluminum deposition by CVD, Cu(hfac)(tmvs) type precursors (where (tmvs) is trimethylvinylsilane and (hfac) is 1,1,1,5,5,5-hexafluoro-2,4-pentanedionate) for thin copper film growth by CVD in addition to aqueous copper containing solutions for either the electroplating or electroless deposition of copper thin films.

Examples of copper and nickel CVD processes are found in U.S. Pat. Nos. 5,085,731; 5,098,516; 5,144,049; 5,187,300; 5,322,712; and U.S. Pat. No. 3,594,216.

In the case of CVD processes there is always a substantial portion of the chemical precursor-that passes through the process chamber unchanged. Typically, this unreacted material, along with the effluent resulting from reacted precursor, must be chemically neutralized or decomposed in an 'abatement system' downstream from the process chamber. The resulting material is then disposed of as toxic chemical waste. Examples of common abatement techniques are pyrolytically destructive 'burn-box' systems, chemically reactive scrubbers and chemical absorbents. The disposal of these waste materials is both expensive and environmentally unsound, especially in the case of copper since it is known to be a heavy metal contaminant. Disposal of copper containing wastes also occurs with the aqueous copper solutions used in electroplating and electroless copper techniques.

Capture of the byproducts of copper CVD has been suggested in the article, Removal of Byproducts from CVD Copper Effluent Streams, No. 41242, Research Disclosures, (August 1998), pp. 1059–1061, where copper hexafluoro-acetylacetonate trimethylvinylsilane ("Cu(hfac)(tmvs)") is the copper CVD precursor which results in copper metal deposition and a by-product mix of unreacted Cu(hfac) (tmvs), Cu(hfac)$_2$ and tmvs. The unreacted Cu(hfac)(tmvs) is converted to Cu(hfac)$_2$ by temperatures of approximately 200° C. to result in an effluent comprised of only Cu(hfac)$_2$ and tmvs. From this mixture solid Cu$^{+2}$(hfac)$_2$ is captured in a cold trap at no greater than 50° C. for reuse.

U.S. Pat. No. 3,356,527 deposits copper from Cu(hfac)$_2$ using hydrogen as a carrier gas and a reducing agent. The resulting Hhfac chelate free ligand is cold trapped and recycled. Similar disclosures are made in: Temple, et. al., Chemical Vapor Deposition of Copper from Copper (II) Hexafluoracetylacetonate, J. Electrochem. Soc. Vol 136, No. 11, November 1989, pp. 3525–3529; Kaloyeros, et. al., Low-Temperature Metal-Organic Chemical Vapor Deposition (LTMOCVD) of Device-Quality Copper Films for Microelectronic Applications, J. Electr. Mat., Vol. 19, No. 3, 1990, pp. 271–276; Van Hemert, et. al. Vapor Deposition of Metals by Hydrogen Reduction of Metal Chelates, J. Electrochem. Soc., Vol. 112, No. 11, November 1965, pp. 1123–1126; and Oehr, et. al., Thin Copper Films by Plasma CVD Using Copper-Hexafluoro-Acetylacetonate, Appl. Phys., A 45, (1988), pp. 151–154.

The present invention overcomes the drawback of abatement and inefficient utilization of chemical components of a copper CVD process by providing a unique process enhancement to recover ligands for reuse and resynthesis of copper CVD precursors as will be set forth in greater detail below.

BRIEF SUMMARY OF THE INVENTION

The present invention is a process for recovering a ligand or mixtures of ligands and/or a metal salt or mixtures of metal salts from a metal-ligand complex byproduct or mixture of metal-ligand complexes of such ligands. This metal-ligand complex or mixture of metal complexes can be the effluent or byproduct from a CVD process whereby metal or metal containing materials are deposited. The effluent is typically a mixture of reaction products and unreacted CVD precursors. The recovery process comprises:

recovering a metal-ligand complex byproduct or a mixture of metal-ligand complexes of such ligands resulting from the deposition of such metal or metal containing materials from a metal-ligand complex precursor or mixture of metal-ligand complex precursors.

contacting such metal-ligand complex byproduct or mixture of metal-ligand complex byproducts of such ligands with a protonation agent; and further recovering such a ligand or ligands free of metals and/or such metal salts free of ligands.

Ligands are thus recovered as the conjugate acid (L$^1$H) of the ligand (L$^1$)$^-$ present in the metal-ligand complex byproduct as an anion.

Preferably, the ligand recovered as the conjugate acid (L$^1$H) of the ligand (L$^1$)$^-$ present in the metal-ligand complex byproduct as an anion is selected from the group comprising:

(a) β-diketones of the formula:

R$^1$C(O)CHR$^2$C(O)R$^3$ where R$^1$ and R$^3$ are alkyl or aryl hydrocarbon or fluorinated alkyl or fluorinated aryl hydrocarbon or silyl substituted alkyl or aryl hydrocarbon or alkoxy or aryloxy groups, R$^2$ is alkyl or aryl hydrocarbon or fluorinated alkyl or fluorinated aryl hydrocarbon or a halogen or hydrogen or alkoxyl or aryloxyl;

(b) β-ketoimines of the formula:

R$^1$C(O)CHR$^2$C(NR$^3$)R$^4$ where R$^1$ and R$^4$ are alkyl or aryl hydrocarbon or fluorinated alkyl or aryl hydrocarbon or silyl substituted alkyl or aryl hydrocarbon or alkoxy or aryloxy, R$^2$ is alkyl or aryl hydrocarbon or fluorinated alkyl or fluorinated aryl hydrocarbon or a halogen, hydrogen, alkoxyl or aryloxyl, R$^3$ is alkyl or aryl hydrocarbon or fluorinated alkyl or fluorinated aryl hydrocarbon or silyl substituted alkyl or aryl hydrocarbon or hydrogen;

(c) β-diimines of the formula:

R$^1$C(NR$^3$)CHR$^2$C(NR$^5$)R$^4$ where R$^1$ and R$^4$ are alkyl or aryl hydrocarbon or fluorinated alkyl or aryl hydrocarbon or silyl substituted alkyl or aryl hydrocarbon or alkoxy or aryloxy groups, R$^2$ is alkyl or aryl hydrocarbon or fluorinated alkyl or fluorinated aryl hydrocarbon or a halogen or alkoxyl or aryloxyl or hydrogen, R$^3$ is alkyl or aryl hydrocarbon or fluorinated alkyl or fluorinated aryl hydrocarbon or hydrogen, $R^5$ is alkyl or aryl hydrocarbon or fluorinated alkyl or fluorinated aryl hydrocarbon or hydrogen; and (d) Ligands of the general formula:

(R)(H)$_n$ where R is an organic or inorganic ligand that bears (n) acidic protons; thus R in a fully deprotonated condition could be a monoanion, dianion, trianion for n=1, n=2, n=3 respectively. In the metal complex [M$^{+x}$][R$^{-n}$]$_y$ where ny=x, R exists as the conjugate base of the acid (R)(H)$_n$. Examples of R for n=1 include, but are not limited to, cyclopentadienyl anion carboxylate anion and amide anion. Examples of R for n=2 include, but are not limited to, 2,4-pentanedione dianion, β-ketoimine dianion, dicarboxylic acid dianion.

More preferably, the metal-ligand complex precursor used in the CVD process from which the CVD effluent will be produced and subsequently processed is a species composed of a first ligand of the type (L$^1$H) coordinated as its conjugate base to a metal ion and a second neutral stabilizing ligand (L$^2$) selected from the group comprising:

(a) Olefins and silylolefins:

(R$^6$)(R$^7$)(C)(C)(R$^8$)(R$^9$) where R$^6$, R$^7$, R$^8$ and R$^9$ can independently be alkyl or aryl hydrocarbon or a substituted silicon group of the type Si(R$^{10}$)$_3$ wherein the R$^{10}$ groups can independently be hydrocarbon alkyl, hydrocarbon aryl or ether groups of the type (O)(R$^{11}$) where R$^{11}$ is selected from alkyl or aryl hydrocarbon; R$^6$ or R$^7$ can be connected to either R$^8$ or R$^9$ by a methylene bridge of the type (CH$_2$)$_n$ where n is 1–4; in the latter case, if any of the connecting groups R$^6$,R$^7$,R$^8$ or R$^9$ are of the silyl substituted type, then their formula becomes Si(R$^{10}$)$_2$(CH$_2$) where the (CH$_2$) unit is a part of the connecting (CH$_2$)$_n$ connecting chain;

(b) alkynes and silylalkynes:

(R$^{12}$)(C)(C)(R$^{13}$) wherein R$^{12}$ and R$^{13}$ are alkyl or aryl hydrocarbons or substituted silicon groups of the type Si(R$^{14}$)$_3$ wherein the R$^{14}$ groups can independently be hydrocarbon alkyl, hydrocarbon aryl or ether groups of the type (O)(R$^{15}$) where R$^{15}$ is selected from alkyl or aryl hydrocarbon;

(c) phospines and phosphites:

P(R$^{16}$)$_3$ where each R$^{16}$ can be individually or mixed alkyl, aryl, fluoroalkyl, fluoroaryl, alkoxy, aryloxy, fluoroalkoxy or fluoroaryloxy; and (d) amines:

N(R$^{17}$)$_3$ where each R$^{17}$ can be individually or mixed alkyl, aryl, fluoroalkyl, fluoroaryl or hydrogen.

Preferably, the metal is selected from Groups 1 through 16 of the Periodic Table of the Elements, including the lanthanide and actinide series. More preferably, the metal or metals are selected from the group comprising transition metals and mixtures thereof. Most preferably, the metal or metals are selected from the group comprising copper, silver, gold, nickel, palladium, platinum, cobalt, rhodium, iridium, ruthenium and mixtures thereof.

In a particular embodiment, the present invention is a process for recovering a ligand or mixtures of ligands of the type (L$^1$H) and (L$^2$) and/or copper salts from a copper-ligand complex byproduct or mixture of copper-ligand complex byproducts of such ligands resulting from the deposition of copper from a copper-ligand complex precursor, comprising:

recovering a copper-ligand complex byproduct or mixture of copper-ligand complex byproducts of such ligands resulting from the deposition of copper from a copper-ligand complex precursor;

contacting the copper-ligand complex byproduct or mixture of copper-ligand complex byproducts of such ligands with a protonation agent; and further recovering the ligands free of copper salts and/or copper salts free of ligands.

In a more specific embodiment, the present invention is a process for recovering a 1,1,1,5,5,5-hexafluoro-2,4-pentanedione ligand from the cupric-ligand complex byproduct, Cu$^{+2}$(1,1,1,5,5,5-hexafluoro-2,4-pentanedionate$^{-1}$)$_2$, comprising:

providing a copper-ligand complex byproduct comprising Cu$^{+2}$(1,1,1,5,5,5-hexafluoro-2,4-pentanedionate$^{-1}$)$_2$ in a process stream;

removing the copper-ligand complex byproduct comprising Cu$^{+2}$(1,1,1,5,5,5-hexafluoro-2,4-pentanedionate$^{-1}$)$_2$ from the process stream;

contacting the copper-ligand complex byproduct comprising Cu$^{+2}$(1,1,1,5,5,5-hexafluoro-2,4-pentanedionate$^{-1}$)$_2$ with a protonation agent selected from the group comprising, but not limited to: sulfuric acid, hydrochloric acid, hydroiodic acid, hydrobromic acid, hydrofluoric acid, trifluoroacetic acid, trifluoromethanesulfonic acid, acetic acid, chloroacetic acid, trichloroacetic acid, nitric acid, sulfurous acid, pentafluorophenol, pentachlorophenol, dicarboxylic acid, fluorinated dicarboxylic acid, fluorinated hydroxy carboxylic acids, perchloric acid, nitrous acid, carboxylic acid, perfluorocarboylic acids, hyroxycarboxylic acids, phosphoric acid, solid acid ion exchange resins, hydrogen sulfide, water and mixtures thereof; and recovering 1,1,1,5,5,5-hexafluoro-2,4-pentanedione.

Preferably, in such specific embodiment of the present invention, recovered 1,1,1,5,5,5-hexafluoro-2,4-pentanedione is further contacted with copper compounds to generate Cu$^{+1}$(1,1,1,5,5,5-hexafluoro-2,4-pentanedionate$^{-1}$).

Preferably, the copper compounds thus used are selected from the group consisting of copper halides, copper oxides copper carboxylates and mixtures thereof.

Preferably, copper is deposited in a chemical vapor deposition from Cu$^{+1}$(1,1,1,5,5,5-hexafluoro-2,4-pentanedionate$^{-1}$) to yield copper metal and the Cu$^{+2}$(1,1,1,5,5,5-hexafluoro-2,4-pentanedionate$^{-1}$)$_2$ in the process stream along with unreacted Cu$^{+1}$ species.

Preferably, the Cu$^{+1}$(1,1,1,5,5,5-hexafluoro-2,4-pentanedionate$^{-1}$) is Cu$^{+1}$(1,1,1,5,5,5-hexafluoro-2,4-pentanedionate$^{-1}$)(trimethylvinylsilane).

In yet another embodiment, the present invention is a process for recovering a 1,1,1,5,5,5-hexafluoro-2,4-pentanedione ligand from a process stream containing a mixture of Cu$^{+1}$(1,1,1,5,5,5-hexafluoro-2,4-pentanedionate$^{-1}$) and Cu$^{+2}$(1,1,1,5,5,5-hexafluoro-2,4-pentanedionate$^{-1}$)$_2$, comprising:

heating the mixture to convert Cu$^{+1}$(1,1,1,5,5,5-hexafluoro-2,4-pentanedionate$^{-1}$) to Cu$^{+2}$(1,1,1,5,5,5-hexafluoro-2,4-pentanedionate$^{-1}$)$_2$ in the process stream;

separating the copper-ligand complex byproduct comprising Cu$^{+2}$(1,1,1,5,5,5-hexafluoro-2,4-pentanedionate$^{-1}$)$_2$ from the process stream;

contacting the copper-ligand complex byproduct comprising Cu$^{+2}$(1,1,1,5,5,5-hexafluoro-2,4-pentanedionate$^{-1}$)$_2$ with a protonation agent; and recovering 1,1,1,5,5,5-hexafluoro-2,4-pentanedione.

Preferably, recovered 1,1,1,5,5,5-hexafluoro-2,4-pentanedione is contacted with a copper containing compound to generate $Cu^{+1}(1,1,1,5,5,5\text{-hexafluoro-2,4pentanedionate}^{-1})$.

Still further preferably, generated $Cu^{+1}(1,1,1,5,5,5\text{-hexafluoro-2,4pentanedionate}^{-1})$ is further reacted with trimethyvinylsilane to produce $Cu^{+1}(1,1,1,5,5,5\text{-hexafluoro-2,4-pentanedionate}^{-1})(\text{trimethylvinylsilane})$.

The protonating agent typically is required to be more acidic (lower $pK_a$) than the ligand being released in its protonated (conjugate acid) form.

Preferably, the protonation agent is selected from, but not limited to, the group consisting of sulfuric acid, hydrochloric acid, hydroiodic acid, hydrobromic acid, hydrofluoric acid, trifluoroacetic acid, trifluoromethanesulfonic acid, acetic acid, chloroacetic acid, trichloroacetic acid, nitric acid, sulfurous acid, pentafluorophenol, pentachlorophenol, dicarboxylic acid, fluorinated dicarboxylic acid, fluorinated hydroxy carboxylic acids, perchloric acid, nitrous acid, carboxylic acid, perfluorocarboylic acids, hyroxycarboxylic acids, phosphoric, solid acid ion exchange resins, hydrogen sulfide, water and mixtures thereof.

BRIEF DESCRIPTION OF SEVERAL VIEWS OF THE DRAWINGS

Not Applicable

DETAILED DESCRIPTION OF THE INVENTION

The present invention provides a process for capture of CVD effluent containing CVD metal-ligand complex byproduct or a mixture of the latter with unreacted CVD metal-ligand complex precursors and the protonation of these components to release their ligands for recycle back to fresh metal precursor. Additionally, the process can be used to recover metal from the metal-ligand complex in the form of metal or metal salts for recycle back to fresh metal precursor or for other purposes. As used in the present invention, the recovered metal-ligand complex byproduct may be the same or different from the metal-ligand complex used as the metal-ligand complex precursor for metal (such as copper) or metal containing materials (such as tantalum nitride) deposition or it may be a mixture of the precursor and the byproduct. In the case of the preferred copper deposition system, the precursor from which copper is deposited is a monovalent metal-ligand complex precursor, while the copper-ligand complex byproduct resulting from the deposition process, i.e., the byproduct of the copper deposition is predominantly a divalent metal complex, although the CVD effluent stream may be a mixture of unreacted monovalent metal-ligand complex precursor and divalent metalligand complex by-product. In other systems a metal-ligand complex precursor may not produce a different metal-ligand complex as a CVD byproduct. As used herein, recovering a ligand is deemed to include mixtures of ligand, and recovering metal is deemed to include metal mixtures and metal salts and mixtures of metal salts, and metal-ligand complex is deemed to include mixtures of metal-ligand complexes. In the present invention, reference to Cu(hfac) and $Cu^{+1}(1,1,1,5,5,5\text{-hexafluoro-2,4pentanedionate}^{-1})$ is understood to include the cuprous-ligand complex where it is associated with a stabilizing additional ligand due to the instability of the cuprous-ligand complex without a stabilizing additional ligand.

Suitable metals are selected from Groups 1 through 16 of the Periodic Table of the Elements, including the lanthanide and actinide series. More preferably, the metal or metals are selected from the group comprising transition metals and mixtures thereof. Most preferably, suitable metals are copper, silver, gold, nickel, palladium, platinum, cobalt, rhodium, ruthenium and iridium. Copper is particularly appropriate to the present invention.

The present invention preferably provides a capture and recovery process for the copper CVD process using Cu(hfac)(tmvs) type precursors that avoids the costly and environmentally compromised 'abatement' technologies described above. The process uses the protonation of the reaction product mixture of the copper CVD process to regenerate the ligands bound in this mixture of copper-ligand complexes. Thus the conjugate acids of the anionic ligands along with the neutral stabilizing ligands in this mixture are released.

Hhfac is an exemplary ($L^1H$) ligand which associates directly with the copper metal as ($L^1$), but other ligands ("$L^1H$") are contemplated by the present invention:

($L^1H$) β-diketones of the formula:
$R^1C(O)CHR^2C(O)R^3$ where $R^1$ and $R^3$ are alkyl or aryl hydrocarbon or fluorinated alkyl or aryl hydrocarbon or silyl substituted alkyl or aryl hydrocarbon or alkoxy or aryloxy groups, $R^2$ is alkyl or aryl hydrocarbon or fluorinated alkyl or aryl hydrocarbon or alkoxyl or aryloxyl or a halogen or hydrogen. Preferably, $R^1$ and $R^3$ are $C_1$ to $C_8$ alkyl or fluoroalkyl. $R^2$ can also be $C_1$ to $C_8$ alkyl or fluoroalkyl, but is preferably hydrogen;

($L^1H$) β-ketoimines of the formula:
$R^1C(O)CHR^2C(NR^3)R^4$ where $R^1$ and $R^4$ are alkyl or aryl hydrocarbon or fluorinated alkyl or aryl hydrocarbon or silyl substituted alkyl or aryl hydrocarbon or alkoxy or aryloxy groups $R^2$ is alkyl or aryl hydrocarbon or fluorinated alkyl or aryl hydrocarbon or alkoxyl or aryloxyl or a halogen or hydrogen, $R^3$ is alkyl or aryl hydrocarbon or fluorinated alkyl or aryl hydrocarbon or hydrogen. Preferably, $R^1$, $R^2$ and $R^4$ are $C_1$ to $C_8$ alkyl or fluoroalkyl. $R^3$ can also be $C_1$ to $C_8$ alkyl or fluoroalkyl, but is preferably hydrogen;

($L^1H$) β-diimines of the formula:
$R^1C(NR^3)CHR^2C(NR^5)R^4$ where $R^1$ and $R^4$ are alkyl or aryl hydrocarbon or fluorinated alkyl or aryl hydrocarbon or silyl substituted alkyl or aryl hydrocarbon or alkoxy or aryloxy groups, $R^2$ is alkyl or aryl hydrocarbon or fluorinated alkyl or fluorinated aryl hydrocarbon or alkoxyl or aryloxyl or a halogen or hydrogen, $R^3$ and $R^5$ are individually alkyl or aryl hydrocarbon or fluorinated alkyl or fluorinated aryl hydrocarbon or hydrogen. Preferably, $R^1$, $R^2$, $R^3$, $R^4$ and $R^5$ are $C_1$ to $C_8$ alkyl or fluoroalkyl. $R^3$ can also be $C_1$ to $C_8$ alkyl or fluoroalkyl; and ($L^1H$) Ligands of the general formula:
$(R)(H)_n$ where R is an organic or inorganic ligand that bears (n) acidic protons; thus R in a fully deprotonated condition could be a monoanion, dianion, trianion for n=1, n=2, n=3 respectively. In the metal complex $[M^{+x}][R^{-n}]_y$ where ny=x, R exists as the conjugate base of the acid $(R)(H)_n$. Examples of R for n=1 include, but are not limited to, cyclopentadienyl anion, carboxylate anion, and amide anion. Examples of R for n=2 include, but are not limited to, 2,4-pentanedione dianion, β-ketoimine dianion.

Tmvs is an exemplary neutral stabilizing ligand, but other stabilizing ligands ("$L^2$") are contemplated:

($L^2$) Olefins and silylolefins:
$(R^6)(R^7)(C)(C)(R^8)(R^9)$ where $R^6$, $R^7$, $R^8$ and $R^9$ can independently be alkyl or aryl hydrocarbon or a substituted silicon group of the type $Si(R^{10})_3$ wherein the $R^{10}$ groups can independently be hydrocarbon alkyl, hydrocarbon aryl or ether groups of the type $(O)(R^{11})$ where $R^{11}$ is selected from alkyl or aryl hydrocarbon. $R^6$ or $R^7$ can also be connected to either $R^8$ or $R^9$ by a methylene bridge of the type $(CH_2)_n$ where n is 1–4. In the latter case, if any of the connecting groups $R^6, R^7, R^8$ or $R^9$ are of the silyl substituted type then their formula becomes $Si(R^{10})_2(CH_2)$ where the $(CH_2)$ unit is a part of the connecting $(CH_2)_n$ connecting chain;

($L^2$) alkynes and silylalkynes:

$(R^{12})(C)(C)(R^{13})$ wherein $R^{12}$ and $R^{13}$ are alkyl or aryl hydrocarbons or substituted silicon groups of the type $Si(R^{14})_3$ wherein the $R^{14}$ groups can independently be hydrocarbon alkyl, hydrocarbon aryl or ether groups of the type $(O)(R^{15})$ where $R^{15}$ is selected from alkyl or aryl hydrocarbon;

($L^2$) phospines and phosphites:

$P(R^{16})_3$ where each $R^{16}$ can be individually or mixed alkyl, aryl, fluoroalkyl, fluoroaryl, alkoxy, aryloxy, fluoroalkoxy or fluoroaryloxy; and ($L^2$) amines:

$N(R^{17})_3$ where each $R^{17}$ can be individually or mixed alkyl, aryl, fluoroalkyl, fluoroaryl or hydrogen.

The present invention provides a simple process by which all of the volatile copper containing species in the process chamber effluent stream can be captured and effectively recycled back into high purity starting materials from which to prepare fresh copper precursor.

It is well known from U.S. Pat. No. 5,144,049 that the Cu(hfac)(tmvs) type of precursors deposit copper films by CVD in a simple thermal process that is driven by chemical disproportionation according to equation (1), shown below. Both the $Cu^{+2}(hfac)_2$ and tmvs byproducts are volatile and thus leave the CVD reactor as vapor.

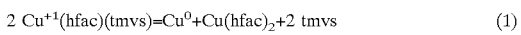

$$2\ Cu^{+1}(hfac)(tmvs) = Cu^0 + Cu(hfac)_2 + 2\ tmvs \qquad (1)$$

Since the copper CVD process using this and related precursors is less than 100% efficient, some of the Cu(hfac)(tmvs) material emerges from the process chamber unreacted, mixed in with $Cu^{+2}(hfac)_2$ and tmvs process effluent. There are a number of ways that this effluent can be captured in a form that permits it to be ultimately recycled into fresh copper precursor.

It has been taught in the Research Disclosures article, cited above, that if this partially unreacted vapor stream is heated to a controlled temperature of approximately 200° C. after it emerges from the CVD process chamber, all of the unreacted portion (i.e., the $Cu^{+1}(hfac)(tmvs)$) will be transformed as per Equation (1) above. Thus the only volatile copper containing species in the resulting effluent stream will be $Cu^{+2}(hfac)_2$. Typically this post-chamber thermal treatment is performed upstream of the main chamber vacuum pump. In this way the CVD chamber pump is only handling $Cu^{+2}(hfac)_2$ and tmvs vapors, which will not corrode the pump or deposit copper metal inside it if its internal temperature is maintained below approximately 200° C. If this $Cu^{+2}(hfac)_2$ and tmvs vapor is then cooled in a suitable trap as it exits the pump, only the $Cu^{+2}(hfac)_2$ will condense out as a stable crystalline solid. Once the trap becomes full, it can then be sealed and removed from the system. Thus no copper containing vapors are released into the environment. Alternatively, the entire sequence of heating the post chamber vapor stream and trapping solid $Cu^{+2}(hfac)_2$ can be carried out upstream of the vacuum pump.

At much lower trapping temperatures, all of the volatiles emerging from the CVD process chamber can be captured, i.e., Cu(hfac)(tmvs), $Cu^{+2}(hfac)_2$ and tmvs, all of which can be subjected to the recycle process.

The preferred embodiments of the present invention show how 1,1,1,5,5,5-hexafluoro-2,4-pentanedione ligand (Hhfac) can be regenerated from solid $Cu^{+2}(hfac)_2$ trapped effluent, which Hhfac can then be chemically treated to regenerate the original copper precursor, in the preferred embodiment, Cu(hfac)(tmvs). The equation for using $H_2SO_4$ as the protonating agent in this Hhfac regenertaion step is:

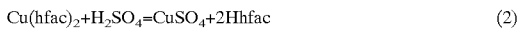

$$Cu(hfac)_2 + H_2SO_4 = CuSO_4 + 2Hhfac \qquad (2)$$

The resulting Hhfac can then be used in a number of different processes to regenerate Cu(hfac).

The Cu(hfac) would be reacted with a stabilizing ligand, such as trimethylvinylsilane (tmvs) in-situ to result in the original copper CVD precursor, Cu(hfac)(tmvs).

This process is compared to the process of U.S. Pat. No. 5,085,731 where the $Cu^{+2}(hfac)_2$ can be directly recycled back into the starting copper precursor by contact with copper metal and tmvs, resulting in etching of the copper metal.

Thus the present invention shows how the copper CVD process using $Cu(L^1)(L^2)$, preferably Cu(hfac)(tmvs), otherwise referred herein as the metal-ligand complex precursor, produces an effluent vapor stream including $Cu^{+2}(hfac)_2$, tmvs and Cu(hfac)(tmvs), otherwise referred herein as the metal-ligand complex byproduct, which can be captured from the effluent and recycled back into pure $(L^1H)$, preferably 1,1,1,5,5,5-hexafluoro-2,4-pentanedione (ie Hhfac) and $(L^2)$ preferably tmvs, which can subsequently be used to synthesize the fresh copper-ligand complex precursor.

In the examples below, pure $Cu^{+2}(hfac)_2$ and alternatively $Cu^{+2}(hfac)_2$ mixed with Cu(hfac)(tmvs) are used to regenerate Hhfac, the latter mixture acting as a model for a low temperature trapping regime whereby unreacted Cu(hfac)(tmvs) and $Cu^{+2}(hfac)_2$ are trapped together as a mixture. Although sulfuric acid is used as the protonation agent in the examples below as the proton source to regenerate the $(L^1H)$ or Hhfac ligand from both $Cu^{+2}(hfac)_2$ and Cu(hfac)(tmvs), other protonation agents, particularly acids could also be used as mentioned previously. The protonation agents of the present invention are by definition chemicals which have a sufficiently acidic free hydrogen proton to be capable of protonating the $(L^1)^-$ anionic ligand of the metal complex, liberating it as its conjugate acid $(L^1H)$ ligand. These protonating agents do not constitute a reducing environment. Hydrogen gas is not included in the definition of acidic protonation agent. Hydrogen is critically different from the protonation agents in that the former can create inadvertant metal plating in the processes contemplated in the present invention, whereas the protonation agents would not; hydrogen gas obviously presents a dangerous operational risk characteristic of gaseous hydrogen. In contrast, the protonation agents of the present invention are safer from an operational perspective and generate CuX salts (X being the conjugate base of the acidic protonation agent) which is more readily removed from the process equipment with a simple water wash and could be used to regenerate copper compounds such as $Cu_2O$ and CuCl for generation of Cu(hfac) species and ultimately the initial copper precursor. The temperature of this protonation step must be temperature controlled to prevent any undesired decomposition of the ligands released. Similarly, altering the temperature of the separated metal species could also lead it to decompose to an undesired metallic deposit.

Other suitable acidic protonation agents include, but are not limited to: sulfuric, hydrochloric, hydroiodic, hydrobromic, hydrofluoric, trifluoroacetic, trifluoromethanesulfonic, acetic, chloroacetic, trichloroacetic, nitric, sulfurous acids. Additionally, suitable protonating agents would be pentafluorophenol, pentachlorophenol, dicarboxylic acids, fluorinated dicarboxylic acids, fluorinated hydroxy carboxylic acids, perchloric acids, nitrous acid, carboxylic acids, hyroxycarboxylic acids, perfluorocarboylic acids phosphoric acid. Solid acid ion exchange resins could also be used such as Nafion ®. In addition, hydrogen sulfide or water, typically as vapor, could be used as the protonation agents. Suitable protonation agents give (in the case of Cu(hfac)(tmvs)) free Hhfac and tmvs, or just Hhfac in the case of $Cu^{+2}(hfac)_2$.

In all of these examples a copper compound would form that would be the salt of the acid used. For instance, hydrogen chloride would yield copper chlorides whereas hydrogen sulfide would yield copper sulfides etc. In the cases of β-diamines and β-ketoimiines and other hydrolytically sensitive ligands, nonaqueous acids are preferred to avoid undesired ligand hydrolysis.

EXAMPLE 1

Liberation of 1,1,1,5,5,5-hexafluoro-2,4-pentanedione (Hhfac) from $Cu^{+2}(hfac)_2$ via ligand protonation with concentrated $H_2SO_4$.

The apparatus used was typical for a basic flask-to-flask transfer of volatiles under vacuum. In an inert atmosphere glovebox, a 500 ml, 3-necked round bottomed flask equipped with a large magnetic stirrer bar was charged with 16.2 g (0.0338 moles) of $Cu^{+2}(hfac)_2$, fitted with a ground glass stopper, a rubber septum and a transfer arm connected to a receiver flask. The apparatus was taken out of the glovebox and transferred to a Schlenk line. The system was then evacuated and backfilled with $N_2$ gas using standard Schlenk line techniques. The flask containing the $Cu^{+2}$ (hfac)$_2$ was cooled to approximately 0° C. using an ice bath, and the receiver flask was cooled in liquid nitrogen before the addition of acid commenced. Concentrated $H_2SO_4$ was added carefully under a purge of $N_2$ (this was done by removing the septum just enough to feed a pipette through the space between the opening septum and the ground glass joint of the flask). As the addition of acid proceeded, the dark blue purple crystals of $Cu^{+2}(hfac)_2$ changed into a very pale blue (almost white) tacky solid. $H_2SO_4$ was added until no remaining color of the starting material was left. At this point, the ice bath was removed from the reaction flask (liquid nitrogen cooling of the receiver vessel was still continued) and the system pumped on under dynamic vacuum (approximately 30 mtorr). Pumping was continued until no further cooling of the reaction vessel was noticed. The receiver flask was allowed to warm to room temperature and the flask containing the colorless liquid product was transferred to an inert atmosphere glovebox, and placed in a vial. The product was identified as Hhfac by Gas Chromatography and Mass Spectrometry. Recovered yield of product was 12.52 g (0.0602 moles, 89% of theoretical). Purity by GC assay was 99.98%.

EXAMPLE 2

Liberation of Hhfac from Cu(hfac)(tmvs)/Cu(hfac)$_2$ mixture via ligand protonation with concentrated $H_2SO_4$.

A similar procedure to Example 1 above was used but with dry ice/isopropyl alcohol used to cool the reaction flask which was charged with 6.5 g (0.0175 moles ) of distilled Cu(hfac)(tmvs) and 6.9 g (0.0144 mol) $Cu^{+2}(hfac)_2$. After the sulfuric acid addition and transfer of volatiles, colorless Hhfac was collected in both the receiver flask and the the liquid nitrogen cooled line trap to the vacuum pump. The product was identified as Hhfac by Gas Chromatography and Mass Spectrometry. Total yield of en recovered product was 7.1 g (0.0341 moles, 74%). Average purity by GC assay was 99.80%.

This reaction was then repeated on a larger scale in an attempt to also capture back the tmvs content of the Cu(hfac) (tmvs):

In an inert atmosphere glovebox, a mixture containing Cu(hfac)$_2$ (10.0 g, 0.02 mol) and Cu(hfac)(tmvs) (10.9 g, 0.03 mol) was placed in a 500 ml two-necked round bottom flask equipped with a stirrer bar. This was connected to a single-neck 250 ml round bottom flask equipped with an teflon valve via a transfer manifold. The reaction flask was then capped with a septum and the whole apparatus removed from the glovebox and taken to a Schlenk line. Using standard Schlenk line techniques the reaction flask was frozen in liquid nitrogen and under an inert gas purge (also $N_2$), excess concentrated $H_2SO_4$ was added via pipette. With the reaction flask contents still frozen, the system was evacuated to base pressure (approximately 30 mtorr) and a static vacuum maintained. The receiver flask then cooled in LN$_2$ and the reaction flask allowed to warm up to room temperature, during which time a pasty pale blue solid and colorless liquid was observed. Once at room temperature the volatile products were trapped over under dynamic vacuum into the receiver flask with stirring in the reaction flask. Once the transfer was complete and the system thawed to room temperature, the colorless liquid volatiles were taken into the glovebox, weighed and submitted for characterization by GC. Yield was 13.8 g. GC revealed the mixture to be Hhfac (96.19%), TMVS (3.49%).

The present invention has been shown to offer a desirable process for recovering ligands and stabilizing ligands from the copper CVD process to recover valuable chemical components of the process in an efficient and effective manner for potential reuse in providing copper CVD precursors. The process also overcomes the problem of abatement or disposal of chemical byproducts and attendant problems with corrosion and plating of process equipment.

The present invention has been set forth with regard to several preferred embodiments, however, the full scope of the present invention should be ascertained from the claims which follow.

We claim:

1. A process for recovering a ligand and/or a metal salt from a metal-ligand complex byproduct resulting from the deposition of such metal or metal containing materials from a metal-ligand complex precursor, comprising:

recovering a metal-ligand complex byproduct resulting from the deposition of a metal from a metal-ligand complex precursor;

contacting said metal-ligand complex byproduct with a protonation agent; and further recovering said ligand free of metal and/or said metal salt free of ligand.

2. The process of claim 1 wherein said ligand is selected from the group consisting of:

(a) β-diketones of the formula:
$R^1C(O)CHR^2C(O)R^3$ where $R^1$ and $R^3$ are alkyl, aryl, fluorinated alkyl, fluorinated aryl, silyl substituted alkyl, silyl substituted aryl, alkoxy or aryloxy groups, $R^2$ is alkyl, aryl, fluorinated alkyl, fluorinated aryl, alkoxy, aryloxy, a halogen or hydrogen;

(b) β-ketoimines of the formula:
$R^1C(O)CHR^2C(NR^3)R^4$ where $R^1$ and $R^4$ are alkyl, aryl, fluorinated alkyl, fluorinated aryl, silyl substituted alkyl, silyl substituted aryl, alkoxy or aryloxy groups, $R^2$ is alkyl, aryl or fluorinated alkyl or fluorinated aryl or alkoxy or aryloxy or a halogen or hydrogen, $R^3$ is alkyl or aryl, fluorinated alkyl, fluorinated aryl, silyl substituted alkyl or silyl substituted aryl or hydrogen;

(c) β-diimines of the formula:

$R^1C(NR^3)CHR^2C(NR^5)R^4$ where $R^1$ and $R^4$ are alkyl or aryl or fluorinated alkyl, fluorinated aryl, silyl substituted alkyl, silyl substituted aryl, alkoxy or aryloxy groups, $R^2$ is alkyl, aryl, fluorinated alkyl, fluorinated aryl, halogen, alkoxy, aryloxy or hydrogen, $R^3$ is alkyl, aryl, fluorinated alkyl, fluorinated aryl or hydrogen, $R^5$ is alkyl, aryl, fluorinated alkyl, fluorinated aryl or hydrogen; and (d) Ligands of the general formula:

$(R)(H)_n$ where R is an organic or inorganic ligand that bears (n) acidic protons, in which in the metal complex $[M^{+x}][R^{-n}]_y$, where ny=x and R exists as the conjugate base of the acid $(R)(H)_n$.

3. The process of claim 1 wherein the ligand is a mixture of a first ligand and a second stabilizing ligand selected from the group consisting of:

(a) Olefins and silylolefins;

$(R^6)(R^7)(C)(C)(R^8)(R^9)$ where $R^6$, $R^7$, $R^8$ and $R^9$ can independently be alkyl, aryl, a substituted silicon group of the type $Si(R^{10})_3$ wherein the $R^{10}$ groups can independently be alkyl, aryl or ether groups of the type $(O)(R^{11})$ where $R^{11}$ is selected from alkyl or aryl; $R^6$ or $R^7$ can be connected to either $R^8$ or $R^9$ by a methylene bridge of the type $(CH_2)_n$ where n is 1–4; in the latter case, if any of the connecting groups $R^6, R^7, R^8$ or $R^9$ are of the silyl substituted type, then their formula becomes $Si(R^{10})_2(CH_2)$ where the $(CH_2)$ unit is a part of the connecting $(CH_2)_n$ connecting chain;

(b) alkynes and silylalkynes:

$(R^{12})(C)(C)(R^{13})$ wherein $R^{12}$ and $R^{13}$ are alkyl, aryl or substituted silicon groups of the type $Si(R^{14})_3$ wherein the $R^{14}$ groups can independently be alkyl, aryl or ether groups of the type $(O)(R^{15})$ where $R^{15}$ is selected from alkyl or aryl;

(c) phospines and phosphites:

$P(R^{16})_3$ where each $R^{16}$ can be individual or mixed alkyl, aryl, fluoroalkyl, fluoroaryl, alkoxy, aryloxy, fluoroalkoxy or fluoroaryloxy; and (d) amines:

$N(R^{17})_3$ where each $R^{17}$ can be individually or mixed alkyl, aryl, fluoroalkyl, fluoroaryl or hydrogen.

4. The process of claim 1 wherein said metal is selected from the group consisting of Groups 1–16 metals within the Periodic Table of the Elements and mixtures thereof.

5. The process of claim 4 wherein said metal is selected from the group consisting of transition metals and mixtures thereof.

6. The process of claim 5 wherein said metal is selected from the group consisting of copper, silver, gold, nickel, palladium, platinum, cobalt, rhodium, iridium, ruthenium and mixtures thereof.

7. A process for recovering a ligand and/or a copper salt from a copper-ligand complex byproduct of such ligand resulting from the deposition of copper from a copper-ligand precursor, comprising:

recovering a copper-ligand complex byproduct resulting from the deposition of copper from a copper-ligand complex precursor;

contacting said copper-ligand complex byproduct with a protonation agent; and recovering said ligand free of copper salts and/or copper salts free of said ligand.

8. A process for recovering a 1,1,1,5,5,5-hexafluoro-2,4-pentanedione ligand from a copper-ligand complex byproduct of $Cu^{+2}(1,1,1,5,5,5\text{-hexafluoro-2,4-pentanedionate}^{-1})_2$, comprising:

providing a copper-ligand complex byproduct of $Cu^{+2}(1,1,5,5,5\text{-hexafluoro-2,4-pentanedionate}^{-1})_2$ in a process stream;

separating said copper-ligand complex byproduct of $Cu^{+2}(1,1,1,5,5,5\text{-hexafluoro-2,4-pentanedionate}^{-1})_2$ from said process stream;

contacting said copper-ligand complex byproduct of $Cu^{+2}(1,1,1,5,5,5\text{-hexafluoro-2,4-pentanedionate}^{-1})_2$ with a protonation agent selected from the group consisting of: sulfuric acid, hydrochloric acid, hydroiodic acid, hydrobromic acid, hydrofluoric acid, trifluoroacetic acid, trifluoromethanesulfonic acid, acetic acid, chloroacetic acid, trichloroacetic acid, nitric acid, sulfurous acid, pentafluorophenol, pentachlorophenol, dicarboxylic acid, fluorinated dicarboxylic acid, fluorinated hydroxy carboxylic acids, perchloric acid, nitrous acid, carboxylic acid, perfluorocarboylic acids, hyroxycarboxylic acids, phosphoric acid, solid acid ion exchange resins, hydrogen sulfide, water and mixtures thereof; and recovering 1,1,1,5,5,5-hexafluoro-2,4-pentanedione.

9. The process of claim 8 wherein recovered 1,1,1,5,5,5-hexafluoro-2,4-pentanedione is further contacted with copper compounds to generate $Cu^{+1}(1,1,1,5,5,5\text{-hexafluoro-2,4-pentanedionate}^{-1})$.

10. The process of claim 9 wherein said copper compound is selected from the group consisting of copper carboxylate, copper halides, copper oxides and mixtures thereof.

11. The process of claim 9 wherein copper is deposited in a chemical vapor deposition from $Cu^{+1}(1,1,1,5,5,5\text{-hexafluoro-2,4-pentanedionate}^{-1})$ to yield copper metal and said $Cu^{+2}(1,1,1,5,5,5\text{-hexafluoro-2,4-pentanedionate}^{-1})_2$ in said process stream.

12. The process of claim 11 wherein said $Cu^{+1}(1,1,1,5,5,5\text{-hexafluoro-2,4-pentanedionate}^{-1})$ is $Cu^{+1}(1,1,1,5,5,5\text{-hexafluoro-2,4-pentanedionate}^{-1})(\text{trimethylvinylsilane})$.

13. A process for recovering a 1,1,1,5,5,5-hexafluoro-2,4-pentanedione ligand from a process stream containing a mixture of $Cu^{+1}(1,1,1,5,5,5\text{-hexafluoro-2,4pentanedionate}^{-1})$ and $Cu^{+2}(1,1,1,5,5,5\text{-hexafluoro-2,4-pentanedionate}^{-1})_2$, comprising:

heating said mixture to convert $Cu^{+1}(1,1,1,5,5,5\text{-hexafluoro-2,4-pentanedionate}^{-1})$ to $Cu^{+2}(1,1,1,5,5,5\text{-hexafluoro-2,4-pentanedionate}^{-1})_2$ in said process stream;

separating said $Cu^{+2}(1,1,1,5,5,5\text{-hexafluoro-2,4-pentanedionate}^{-1})_2$ from said process stream;

contacting said $Cu^{+2}(1,1,1,5,5,5\text{-hexafluoro-2,4-pentanedionate}^{-1})_2$ with a protonation agent; and recovering 1,1,1,5,5,5-hexafluoro-2,4-pentanedione.

14. The process of claim 13 wherein recovered 1,1,1,5,5,5-hexafluoro-2,4-pentanedione is contacted with a copper containing compound to generate $Cu^{+1}(1,1,1,5,5,5\text{-hexafluoro-2,4-pentanedionate}^{-1})$.

15. The process of claim 14 wherein generated $Cu^{+1}(1,1,1,5,5,5\text{-hexafluoro-2,4-pentanedionate}^{-1})$ is formed in situ with trimethyvinylsilane to produce $Cu^{+1}(1,1,1,5,5,5\text{-hexafluoro-2,4-pentanedionate}^{-1})(\text{trimethylvinylsilane})$.

16. The process of claim 13 wherein said protonation agent is selected from the group consisting of sulfuric acid, hydrochloric acid, hydroiodic acid, hydrobromic acid, hydrofluoric acid, trifluoroacetic acid, trifluoromethanesulfonic acid, acetic acid, chloroacetic acid, trichloroacetic acid, nitric acid, sulfurous acid, pentafluorophenol, pentachlorophenol, dicarboxylic acid, fluorinated dicarboxylic acid, fluorinated hydroxy carboxylic acids, perchloric acid, nitrous acid, carboxylic acid, perfluorocarboylic acids, hyroxycarboxylic acids, phosphoric acid, solid acid ion exchange resins, hydrogen sulfide, water and mixtures thereof.

* * * * *